United States Patent [19]
Oberhoffner et al.

[11] Patent Number: 6,048,947
[45] Date of Patent: Apr. 11, 2000

[54] TRIBLOCK TERPOLYMER, ITS USE FOR SURGICAL SUTURE MATERIAL AND PROCESS FOR ITS PRODUCTION

[75] Inventors: Sven Oberhoffner, Weinstadt-Benzach; Heinrich - Ing. Planck, Nuertingen, both of Germany

[73] Assignee: Deutsche Institute fuer Textil- und Faserforschung Stuttgart Stiftung des Oeffentlichen Rechts, Denkendorf, Germany

[21] Appl. No.: 08/947,198

[22] Filed: Oct. 8, 1997

[30] Foreign Application Priority Data

Aug. 10, 1996 [DE] Germany .............................. 196 41 335

[51] Int. Cl.⁷ .................................................... A61L 17/12
[52] U.S. Cl. .......................... 525/411; 525/413; 525/415; 528/354; 606/230
[58] Field of Search ..................................... 525/411, 413, 525/415; 528/354; 606/230

[56] References Cited

U.S. PATENT DOCUMENTS

| | | | |
|---|---|---|---|
| 3,839,524 | 10/1974 | Adams et al. | 264/131 |
| 3,847,156 | 11/1974 | Trumble | 128/335.5 |
| 4,377,010 | 3/1983 | Fydelor et al. | 3/1.4 |
| 4,429,080 | 1/1984 | Casey et al. | 525/415 |
| 4,675,361 | 6/1987 | Ward, Jr. | 525/92 |
| 4,686,137 | 8/1987 | Ward, Jr. | 428/290 |
| 4,857,602 | 8/1989 | Casey et al. | 525/408 |
| 4,861,830 | 8/1989 | Ward, Jr. | 525/92 |
| 4,933,430 | 6/1990 | Kessler et al. | 528/323 |
| 4,990,158 | 2/1991 | Kaplan et al. | 623/1 |
| 5,047,048 | 9/1991 | Bezwada et al. | 606/231 |
| 5,120,802 | 6/1992 | Mares | 525/415 |
| 5,133,739 | 7/1992 | Bezwada et al. | 606/230 |
| 5,236,444 | 8/1993 | Muth et al. | 606/230 |
| 5,321,113 | 6/1994 | Cooper et al. | 528/176 |
| 5,378,801 | 1/1995 | Reichert et al. | 528/354 |
| 5,403,347 | 4/1995 | Roby et al. | 606/230 |
| 5,411,554 | 5/1995 | Scopelianos et al. | 623/8 |
| 5,431,679 | 7/1995 | Bennett et al. | 606/230 |
| 5,468,253 | 11/1995 | Bezwada et al. | 606/230 |
| 5,522,841 | 6/1996 | Roby et al. | 606/230 |
| 5,525,646 | 6/1996 | Lundgren et al. | 523/105 |
| 5,550,172 | 8/1996 | Regula et al. | 523/118 |
| 5,554,170 | 9/1996 | Roby et al. | 606/230 |
| 5,610,266 | 3/1997 | Buchholz | 528/354 |
| 5,641,502 | 6/1997 | Skalla et al. | 424/426 |
| 5,695,879 | 12/1997 | Goldmann et al. | 428/364 |
| 5,713,920 | 2/1998 | Bezwada et al. | 606/230 |
| 5,854,383 | 12/1998 | Erneta et al. | 528/354 |

FOREIGN PATENT DOCUMENTS

| | | |
|---|---|---|
| 0 098 394 A1 | 1/1984 | European Pat. Off. . |
| 0 441 322 A1 | 8/1991 | European Pat. Off. . |
| 0 626 404 A2 | 11/1994 | European Pat. Off. . |
| 0 711 548 | 5/1996 | European Pat. Off. . |
| 0 711 794 | 5/1996 | European Pat. Off. . |
| 0 719 811 | 7/1996 | European Pat. Off. . |
| 0 747 072 | 12/1996 | European Pat. Off. . |
| 0 908 482 A1 | 4/1999 | European Pat. Off. . |
| 43 00 420 | 5/1994 | Germany . |
| 1 571 108 | 9/1980 | United Kingdom . |
| 1 588 031 | 4/1981 | United Kingdom . |
| 2122228 | 11/1984 | United Kingdom . |
| 2159846 | 12/1985 | United Kingdom . |
| WO 94/11441 | 5/1994 | WIPO . |
| WO 96/41526 | 12/1996 | WIPO . |

OTHER PUBLICATIONS

M. Roller et al., "Liquid and low melt absorbable copolymers and their blends", Annual Tech. Conf. —SPE, 54th (vol. 3) pp. 2848–2851 (1996)—Abstract.

*Primary Examiner*—Patricia A. Short
*Attorney, Agent, or Firm*—Pennie & Edmonds LLP

[57] ABSTRACT

A triblock terpolymer with a structure ABA formed from a biodegradable hard segment A and a biodegradable soft segment B has as the soft segment a statistical terpolymer with a completely amorphous structure. A process for its production comprises chemically reacting the hard segment monomer with hydroxy terminal groups of the soft segment B. The absorbable polymer is suitable for the production of a surgical suture material, which is wholly or partly formed from the polymer.

13 Claims, No Drawings

TRIBLOCK TERPOLYMER, ITS USE FOR SURGICAL SUTURE MATERIAL AND PROCESS FOR ITS PRODUCTION

TECHNICAL FIELD

The present invention relates to a triblock terpolymer of absorbable synthetic polymer, its use in surgical suture material and processes for the production thereof.

BACKGROUND OF THE INVENTION

Absorbable synthetic polymers usable for medical products such as e.g. surgical suture material or implants, include conventional homopolymers of polyglycolic acid or polylactic acid, as well as their copolymers. Particularly in the case of suture materials monofilament products have the advantage compared with braided multifilament structures, that they have a smooth, homogeneous surface. This facilitates the course of the thread and reduces the occurrence of capillarities. Thus, no coatings need be applied in order to improve the compactness of the thread and the pull-through forces through the tissue to be sewn are reduced due to the smooth structure.

A disadvantage of the known polymers for suture material is their high flexural strength, partly linked with an inadequate transverse tensile strength, which leads to a poor knotting behaviour and limits the use for surgical sutures.

Therefore developments have led to the use of block copolymers, e.g. the structure AB, ABA or ABAB, in which at least one block constitutes a so-called soft segment. It is known to produce soft segments by homopolymerization or copolymerization of monomers, such as e.g. trimethylene carbonate (1,3-dioxan-2-one) TMC, ε-caprolactone or p-dioxanone (1,4-dioxan-2-one). The soft segments are reacted with hard segments, whose monomers are typically chosen from glycolide and/or lactide, to the corresponding block copolymers.

Among the commercially marketed long term-absorbable suture materials reference is made to the block copolymer of glycolide and trimethylene carbonate disclosed in European patent 98394 A1 of the American Cyanamid Company. A crystalline copolymer of glycolide and ε-caprolactone described in European patent EP 441322 A1 of ETHICON Inc. constitutes a short term-absorbable polymer material.

European patent EP 626404 A2 of United States Surgical Corporation (USSC) claims absorbable block copolymers of glycolide, p-dioxanone and trimethylene carbonate, in which the soft segment is formed solely from p-dioxanone and TMC.

U.S. Pat. No. 5,431,679 of United States Surgical Corporation describes a block copolymer, which comprises a block of glycolide ester units and a block of statistical copolymers of 1,3-dioxan-2-one and caprolactone.

SUMMARY OF THE INVENTION

The problem of the present invention is to provide an absorbable synthetic polymer in the form of a triblock terpolymer, which has a good degradation and absorption behaviour in vivo combined with good mechanical characteristics, which is easy and inexpensive to manufacture and which can be easily and reliably used for surgical suture material.

This problem is solved by a triblock terpolymer with a structure ABA of a biodegradable hard segment A and a biodegradable soft segment B, in which the soft segment B is dihydroxy-terminated and to it is chemically bound both hard segments and which is characterized in that the soft segment is a statistical terpolymer with a completely amorphous structure.

The completely amorphous structure of the soft segment can advantageously influence the in vivo degradability. The degradation behaviour of the soft segment approaches that of the hard segment in that it also contains the rapidly degradable glycolide. As a result of its completely amorphous nature, it has surprisingly been found that there is a relatively rapid degradation behaviour, which can be attributed to a faster diffusion of the hydrolysis solution or the body fluids than can be the case in crystalline ranges. With regards to the structural features there is also an increased compatibility of soft segment and hard segment. This leads to a balanced absorption behaviour in vivo of the hard and soft segments in the triblock terpolymer.

The structure of the triblock terpolymers according to the invention has an advantageous effect on the characteristics of products produced there-from. Examples are favourable mechanical characteristics such as good flexibility, e.g. low flexural strength, good modulus behaviour and good knotting characteristics, such as are in particular desired in applications in the medical sector, such as for surgical sewing or suture threads.

DETAILED DESCRIPTION OF THE INVENTION

In the triblock terpolymer according to the invention the hard segment A can in particular be a homopolymer. In the case of the triblock terpolymer the terpolymer in the soft segment B can contain a monomer, which is contained in the hard segment A. Advantageously, in the block terpolymer, the percentage of hard segment blocks A is 20 to 95 wt. %, particularly 20 to 80%, preferably 40 to 60 wt. % of the triblock terpolymer and the residue is soft segment B.

The triblock terpolymer in the soft segment B can be characterized in that it is formed from trimethylene carbonate, ε-caprolactone and glycolide. In particular, trimethylene carbonate can be contained in a percentage of 5 to 70 wt. %, ε-caprolactone in a percentage of 5 to 70 wt. % and glycolide in a percentage of 10 to 70 wt. % in the terpolymer according to the invention. The percentages by weight of the components trimethylene carbonate, ε-caprolactone and glycolide are chosen in such a way that together they represent 100 wt. % of the terpolymer in the soft segment B. According to the invention, the triblock polymer in the terpolymer preferably contains 10 to 40 wt. % trimethylene carbonate, 10 to 40 wt. % ε-caprolactone and 30 to 60 wt. % glycolide.

In the terpolymer of the soft segment B according to the invention can be present trimethylene carbonate and ε-caprolactone in a weight ratio between 80:20 and 20:80, particularly 70:30 and 30:70. The soft segment terpolymer preferably contains trimethylene carbonate and ε-caprolactone in a weight ratio of 50:50. In another embodiment the soft segment terpolymer can contain ε-caprolactone in a higher proportion than trimethylene carbonate.

The triblock terpolymer according to the invention is in particular characterized in that the monomer present both in the hard segment A and the soft segment B is glycolide. Preferably the terpolymer of the soft segment B is produced by statistical copolymerization of trimethylene carbonate, ε-caprolactone and glycolide.

In the triblock terpolymer according to the invention advantageously the soft segment B, as the middle block, is surrounded on either side by hard segment blocks A. The hard segment is attached to both ends of the soft segment by polymerization reaction at the OH-groups. The formation of the hard segment can advantageously take place by reacting the OH-terminated soft segment terpolymer with glycolide monomers. A triblock terpolymer strand according to the invention preferably comprises only one soft segment in the polymer strand.

Tests of the physical and physiological characteristics of the triblock terpolymer according to the invention were performed, such as e.g. relative to the microstructure, the glass transition range, the melting behaviour and the inherent viscosity, as well as the in vitro and in vivo degradation and the absorption behaviour. Unless stated otherwise viscosity measurements take place in hexafluoroisopropanol (HFIP) at 30° C. and a concentration of c=0.8 g/dl. Measurements of the glass transition temperatures (Tg), melting points (Tm) and melting enthalpies (Hm) are performed by differential scanning calorimetry (DSC) at a scanning rate of 10° C./min. The in vitro degradation was measured in the Sorensen buffer at pH 7.4 and a temperature of 37° C. and given as a percentage retention relative to the original knot breaking strength.

The triblock terpolymer according to the present invention differs from the conventional block polymers hitherto used e.g. for the production of surgical suture material as a result of the modified sequence of the monomer units in the macromolecular chain. This also influences the interactions between the individual chain molecules in a filament formed. As is well known to experts in the fibre technology field, the physical and mechanical characteristics of a fibre are dependent on the orientation and structure of the chain molecules, particularly the formation of amorphous and crystalline ranges. Preferably, the triblock terpolymer has an inherent viscosity of 0.5 to 1.5 dl/g, particularly 0.7 to 1.2 dl/g. The triblock terpolymer according to the invention can also have a glass transition temperature or point between −10° C. and +25° C. Preferably, the soft segment B in the triblock terpolymer according to the invention has a glass transition point between −30° C. and +10° C. In particular, the triblock terpolymer is characterized in that its structure is partly crystalline, the crystallinity being limited to the hard segment. The melting enthalpy, a measure for the crystallinity of a polymer, in the case of the triblock terpolymer according to the invention is between 15 and 60 J/g, particularly between 15 and 50 J/g.

The absorbable triblock terpolymer according to the invention is advantageously characterized by an accelerated absorbability in living tissue. Its in vitro degradation time can be 5 to 30 days (Sorensen buffer, 37° C.).

It is to be assumed that the incorporation of a third monomer in random distribution in the soft segment reduces the crystallization tendency of the soft segment. In fact, tests by differential scanning calorimetry (DSC), reveals that/the soft segment B is completely amorphous in the structure. A suppression of the crystallization in the soft segment leads to a desired improvement to the flexibility of products produced from the triblock terpolymer according to the invention. Measured values relative to the mechanical characteristics of extruded filaments in two preferred embodiments of the inventive polymer are given in tables 1 and 2.

The degradation of the polymer according to the invention takes place in the body of an animal or human by metabolic processes. Body and tissue fluids participate in the reaction. As a result of hydrolysis the polymer chain is split up into smaller and more readily soluble fragments. The fragments are then further degraded, optionally accompanied by the participation of enzymatic processes. The degradation products are transported away by the metabolic system and, in the same way as other metabolic waste products, are eliminated from the organism. It is important for a good compatibility of the absorbable suture material with respect to the patient, that during the degradation process no harmful metabolites are formed or concentrated. Polyglycolic acid is in particular characterized that during its decomposition in vivo no toxic decomposition products are formed. The trimethylene carbonate and caprolactone used as comonomers according to the invention are also characterized by a good compatibility and the avoidance of toxic reactions.

Compared with glycolide, trimethylene carbonate and caprolactone have much longer degradation times. This can lead to a widely differing absorption behaviour of hard segment (e.g. glycolide) and soft segment (e.g. TMC/caprolactone copolymer according to the prior art). Incompatible polymers or polymer segments have a phase separation tendency, which, as can be gathered from table 2, surprisingly leads to a deterioration of the mechanical strength.

By polymerizing glycolide into the soft segment it is possible to increase the compatibility between the hard segment and the soft segment. This has an advantageous effect on the mechanical characteristics of the polymer important in practice. This can also lead to a more uniform degradation and absorption of the soft and hard segments of the block copolymers in the living organism.

The degradation behaviour of the triblock terpolymer according to the invention can be modified by varying the overall glycolide percentage in the polymer. The degradation behaviour of the triblock terpolymer according to the invention can also be modified by varying the percentage of soft segment B in the triblock terpolymer (cf. table 3). Another influencing factor, through whose variation it is possible to modify the degradation behaviour in the inventive polymer, is the intensity and duration of any γ radiation. Treatment with γ rays can be linked with a partial molecular weight deterioration, which leads to shortened degradation times. It is possible in this way to adapt the characteristics of the triblock terpolymer according to the invention to the advantageous requirements in the individual case. In a possible embodiment of the invention, a sterilization performed with the aid of γ rays can be simultaneously used for controlling the degradation behaviour of the surgical suture materials produced from the polymer according to the invention.

It has been found that the triblock terpolymer with a structure ABA formed from a hard segment A of biodegradable monomer and a soft segment B of biodegradable monomer, in which the soft segment is a statistical dihydroxyterminated terpolymer with an amorphous structure, is suitable as an absorbable polymer for producing a surgical suture material. The product provided for medical use is then advantageously wholly or partly formed from the polymer.

It has surprisingly been found that surgical suture materials can be produced from the block polymer according to the invention, particularly monofilaments for suture material, which have the very good characteristics necessary for surgical material, particularly with respect to the physical properties and practical handling.

As is apparent from the above description of the characteristics of the polymer according to the invention, it is in particular characterized by its biodegradability and favourable degradation behaviour, together with its good mechanical characteristics, especially its flexibility, for applications in the medical sector.

Advantageously, surgical suture material of absorbable synthetic polymer in the form of a monofilament formed from the triblock terpolymer of glycolide, trimethylene carbonate and caprolactone is suitable for use for wound closure with accelerated absorption. The aforementioned advantageous mechanical characteristics of monofilament suture or sewing threads of triblock terpolymer allow an easy handling of the suture material during the sewing of tissue in an animal or human body, e.g. when fixing organs, closing tears in the body tissue or closing surgical incisions. In particular, due to the formation of a monofilament with a smoother thread surface than a multifilament suture thread, the tissue to be treated can be protected against damage caused by suture insertion. This limits the risk of patient-prejudicial side-effects, such as e.g. delayed healing and tissue granuloma formation. A good knotability and knot strength in conjunction with a high initial tensile strength and flexibility allow a reliable fixing and stabilization of the linked wound edges during the first days following a surgical operation. In particular, during these first days, regenerative, endogenous tissue can reliably be used for natural wound healing, because the risk of tearing apart of the wound edges during movement of the patient is reduced as a result of the secure and reliable fixing.

The present invention also provides a process for the production of a triblock terpolymer with a structure ABA formed from a hard segment A of biodegradable monomer and a soft segment B of biodegradable monomer, which is characterized in that the triblock terpolymer is formed by chemically reacting the hard segment monomer with hydroxy terminal groups of the soft segment B, which is a statistical, dihydroxy-terminated terpolymer with an amorphous structure.

More particularly, in the case of the production process according to the invention, the soft segment can be produced by statistical copolymerization of trimethylene carbonate, ε-caprolactone and glycolide, with 5 to 70, preferably 10 to 40 wt. % trimethylene carbonate, 5 to 70, preferably 10 to 40 wt. % ε-caprolactone and 10 to 70, preferably 30 to 50 wt. % glycolide. The percentages by weight of the components trimethylene carbonate, ε-caprolactone and glycolide are chosen in such a way that, together, they represent 100 wt. % of the terpolymer in the soft segment B.

The monomer mixture for producing the soft segment according to the invention can have added to it in the conventional necessary quantity, a suitable catalyst, such as e.g. tin octoate, as well as a bifunctional initiator, e.g. diethylene glycol. The reaction is performed as a melt polymerization at temperatures above 150° C. in a suitable heatable reactor equipped with a stirrer. In particular, this polymerization reactor must be designed in such a way that the resulting highly viscous melts are homogenized, the requisite temperature ranges can be respected and the raw polymer can be substantially completely discharged from the reactor.

The terpolymerization reaction can be performed according to standard procedures, known to the expert, for the production of statistical copolymers. Preferably, the reaction mixture is heated, accompanied by constant thorough mixing, particularly to a temperature of 190 to 210° C., preferably 205° C. For the duration of the reaction, an overpressure of 1 to 2 and preferably 1.5 bar argon is applied. For a reaction duration of 2 to 6 hours, preferably 5 hours, the preintroduced monomers can react to a statistical terpolymer. Advantageously, the process is characterized in that the reaction rate during soft segment polymerization is above 95%.

In an embodiment of the process according to the invention, the soft segment can be isolated after polymerization and reacted to the triblock terpolymer following repeated melting on with glycolide. For this purpose, at the end of the reaction, the raw terpolymer of the soft segment B is discharged as melt and comminuted after cooling.

The reaction of the soft segment terpolymer with glycolide monomer to the triblock terpolymer takes place in known manner as a melt polymerization in a suitable polymerization reactor, as described hereinbefore for the production of the soft segment. Once again it is possible to add in the standard, necessary quantity a suitable catalyst, e.g. tin octoate, as well as a bifunctional initiator, e.g. diethylene glycol. Preferably, the reaction mixture is heated for a period of 0.5 to 1 hour to a temperature of 200 to 250° C., preferably 220 to 240° C. The switching in of a stirrer preferably takes place after reaching a temperature of approximately 130° C. For the duration of the reaction an overpressure of 1 to 2 and preferably 1.5 bar argon is applied. During the reaction period of 1 to 3 hours, the triblock terpolymer with hard and soft segments of structure ABA is formed. Subsequently the polymer is discharged from the reactor and, after cooling, is comminuted and dried in the usual way.

In another embodiment of the process according to the invention, after polymerization the soft segment can be directly reacted in situ with glycolide to the triblock terpolymer. The in situ polymerization of the triblock terpolymer according to the invention takes place as melt polymerization in a polymerization reactor, as described hereinbefore for the aforementioned polymerization reactions. Firstly the monomers glycolide, 1,3-dioxan-2-one and caprolactone are added to the reactor in the quantities necessary for soft segment formation, together with the necessary catalyst and initiator. Accompanied by stirring, the mixture is heated at an argon overpressure of 1 to 2 bar for approximately 30 min to a temperature of 200 to 210° C. and is reacted under these conditions for 4 to 6 hours. For forming the triblock terpolymer, a requisite quantity of the hard segment monomer glycolide is added as melt. Reaction for hard segment formation takes place under an argon counterflow and accompanied by vigorous stirring. The temperature is increased in less than 15 min to approximately 230° C., is then reduced to approximately 220° C. and these conditions are maintained until the reaction is completed for approximately 1 to 2 hours. The finished triblock terpolymer is discharged and, after cooling, comminuted and dried in the conventional manner.

Using conventional melt spinning processes, products for use as absorbable surgical suture materials can be produced from the triblock terpolymers according to the invention. The triblock terpolymer can be extruded to filaments in one embodiment of the process. In a preferred embodiment the triblock terpolymer can be extruded in a melt spinning process, e.g. a single-screw or a twin-screw extruder, through suitable spinning nozzles to monofilaments. In the case of melt spinning the nozzle temperature is in particular up to 30° C. above the melting point of the processed polymer.

Advantageously, for strengthening purposes, the filament formed is extruded in a cooling bath, which contains water or a conventional organic liquid, such as e.g. glycerin. The cooling bath temperature can be in the range 2 to 60° C., particularly 2 to 50° C. Preferably the filament is extruded in water at ambient temperature. The distance between the spinning nozzle and the cooling bath is between 0.5 and 30 cm, preferably between 1 and 10 cm.

In order to obtain the necessary mechanical characteristics, the extruded filament can be stretched or drawn for orienting the molecular chains. The strengthened spinning thread can either be drawn directly or, following winding up or spooling, in a separate step using standard methods. It is possible to carry out drawing either in heated, liquid media such as e.g. water or glycerin baths, or using drawing ovens and rails. Advantageously it can be drawn with a draw ratio of 1:4 to 1:10.

In order to ensure a permanent maintenance of the orientation, the mechanical characteristics and the dimensional stability of the filaments, the stretched or drawn polymer material can be set or fixed by annealing. Setting takes place at temperatures in the range 50 to 150° C., preferably 70 to 130° C. The heat setting process duration is between 1 and 20 hours. Annealing can take place with or without shrinkage of the filament. It is particularly preferable for drawing and heat setting to take place immediately following extrusion, particularly using a combined process. Advantageously, for this purpose, use is made of a corresponding equipment constituted by combined, suitable devices. In a preferred embodiment of the invention monofilament or multifilament products from the triblock terpolymer can be exposed for 1 to 20 hours, with or without shrinkage, to a temperature of 50 to 150° C. in order to obtain dimensional stability.

The diameter of the monofilaments produced in this way can be in the standard range 0.001 to 1.2 mm. Advantageously, the monofilaments according to the invention are characterized by the aforementioned mechanical characteristics.

As examples for uses in medical products mention is made of filaments produced by spinning, which are used directly in the form of monofilaments or multifilament thread structures and employed as surgical suture material absorbable in the organism of the patient.

The polymers and medical products produced therefrom according to the present invention can be dyed or undyed. For dyeing purposes, it is possible to use the dyes authorized for absorbable medical products by the US FDA (Food & Drug Administration), such as e.g. D+C green No. 6, D+C violet No. 2, etc.

Triblock terpolymer filaments produced according to the invention can be processed according to conventional methods to surgical suture material, e.g. cut to suitable lengths. In particular, the polymer material according to the invention can be appropriately sterilized. An appropriate sterilization process can be chosen from conventional physical or chemical methods for inactivating microorganisms, or a combination of such methods. One possible sterilization process comprises treatment with γ radiation. Preferably, sterilization of the inventive polymer material for medical products takes place using ethylene oxide.

Advantageously, surgical suture material produced from the polymer according to the invention, cut to appropriate lengths, can be suitably packed in ready-for-use manner. According to a preferred embodiment, the suture threads according to the invention can be made available already equipped with surgical needles.

Due to the hydrolytic decomposability of the polymer material according to the invention medical products, during the storage thereof, must be protected against moisture and elevated temperatures, so that the strength characteristics are fully maintained up to the time of use. Advantageously, medical suture threads produced according to the invention, are packed in ready-for-use state in dried form. Appropriately this can be brought about by a moisture-proof pack, particularly a pack of moisture-impermeable film material, preferably as a vacuum pack. It is also achievable by the choice of a dry, cool storage location.

The polymers according to the invention and the products produced therefrom are in particular characterized by the following physical properties. It is a semicrystalline triblock polymer, which is consequently solid at ambient temperature and which has a firm consistence. The triblock polymer has a melting point above 120° C. There is no phase separation between the hard and soft segments. This is apparent from the glass transition temperature, Which for the terpolymer according to the invention is −10 to +30° C., particularly 0 to +15° C. With several phases, separate detectable glass transition points would exist.

The inherent viscosity of the triblock terpolymer according to the invention is advantageously above 0.7 dl/g in HFIP (c=0.8g/l at 30° C.). The inherent viscosity can be up to 2.0 dl/g for polymers usable in practice.

So that in the polymer according to the invention the residual monomer content is low and simultaneously a high reaction or transformation rate is obtained, the soft segment polymerization in the melt can take place at over 150° C., preferably above 170° C., up to 235° C.

In the case where the polymer according to the invention is transformed into threads and is in particular drawn or stretched, the knot breaking strength changes during the degradation period. After 7 days it is between 30 and 80%, preferably between 50 and 70% of the original value. After 14 days the knot breaking strength is still between 5 and 50%, particularly between 20 and 40% of the original value, as is apparent from measurements in the Sorensen buffer at pH 7.4 and 37° C.

Moreover, with the drawn polymer material according to the invention, particularly drawn threads, the elongation is between 15 and 60%, preferably between 25 and 45%. The linear tensile strength is between 300 and 1000 N/mm$^2$, particularly above 400 N/mm$^2$. The knot tensile strength is between 250 and 800 N/mm$^2$, preferably above 350 N/mm$^2$.

For the triblock polymer according to the invention the modulus of elasticity is between 500 and 3000 N/mm$^2$, preferably below 1800 N/mm$^2$. In the case of multifilament threads modulus of elasticity values can be up to 7000 l/mm$^2$, preferably less than 5000/mm$^2$.

EXAMPLES

Further features and details of the invention can be gathered from the following description of preferred, exemplified embodiments. The individual features can be implemented individually or in the form of subcombinations. The examples merely serve to illustrate the present invention, which is in no way restricted thereto.

Example 1

Dihydroxy-terminated Soft Segment of Composition G/TMC/CL=30/35/35.

In a reactor are placed 350 g of 1,3-dioxan-2-one (TMG), 350 g of caprolactone (CL) and 300 g of glycolide (G), together with 0.2 g of tin octoate (solution in diethyl ether) and 1 g of diethylene glycol. The ether is then drawn off in high vacuum at 50° C. After 1 hour an overpressure of 1.5 bar argon is applied and the reactor heated to 205° C., accompanied by stirring. This temperature is maintained for 5 hours, after which the polymer is discharged and analyzed. The inherent viscosity is 0.648 dl/g, and the glass transition point −27.5° C.

Example 2
Dihydroxy-terminated Soft Segment of Composition G/TMC/CL=40/30/30.

To a reactor are added 300 g of 1,3-dioxan-2-one, 300 g of caprolactone and 400 g of glycolide, together with 0.2 g of tin octoate (solution in diethyl ether) and 1 g of diethylene glycol. The reaction to the polymer takes place in the same way as in example 1. The inherent viscosity is 0.937 dl/g and the glass transition temperature −19.8° C.

Example 3
Dihydroxy-terminated Soft Segment of Composition G/TMC/CL:=50/25/25.

To a reactor are added 250 g of 1,3-dioxan-2-one, 250 g of caprolactone and 500 g of glycolide, together with 0.2 g of tin octoate (solution in diethyl ether) and 1 g of diethylene glycol. The reaction takes place as in example 1. The inherent viscosity is 0.813 dl/g and the glass transition point −9.3° C.

Example 4
Triblock Terpolymer of Composition G/TMC/CL=72/14/14 with 40 wt. % of soft Segment from Example 1.

To a reactor are added 600 g of glycolide and 400 g of the soft segment of example 1, together with 0.1 g of tin octoate (solution in diethyl ether). The ether is drawn off in high vacuum at 50° C. After applying an over-pressure of 1.5 bar argon, the reactor is heated for 40 min to 240° C. The switching in of a stirrer takes place on reaching a temperature of 130° C. The temperature of 240° C. is maintained for 70 min and the polymer is then discharged. The inherent viscosity of the ABA triblock terpolymer is 0.75 dl/g, the glass transition point is 9.5° C. and the melting point 182.3° C.

Example 5
Triblock Terpolymer of Composition G/TMC/CL=73/13.5/13.5 with 45 wt. % of the Soft Segment of Example 2.

550 g of glycolide and 450 g of the soft segment from example 2, without additional catalyst addition, are placed in the reactor and dried in high vacuum at 60° C. for 16 hours. After applying an overpressure of 1.5 bar argon, the reactor is heated to 235° C. for 35 min, the stirrer being switched in on reaching a temperature of 130° C. The temperature of 235° C. is maintained for 60 min and the polymer is then discharged.

The inherent viscosity of the ABA triblock terpolymer is 1.01 dl/g, the glass transition temperature 9.8° C. and the melting point 180.1° C.

Example 6
Triblock Terpolymer of Composition G/TMC/CL=73/13.5/13.5 with 54 wt. % Soft Segment of Example 3.

460 g of glycolide and 540 g of the soft segment from example 3, together with 0.05 g of tin octoate (solution in diethyl ether) are placed in the reactor and dried in high vacuum for 16 hours at 50° C. After applying an overpressure of 1.5 bar argon, the reactor is heated for 45 min to 230° C., the stirrer being switched in on reaching a temperature of 130° C. After 10 min the temperature is reduced to 220° C. and kept at this level for 100 min. The polymer is then discharged.

The inherent viscosity of the ABA triblock terpolymer is 0.813 dl/g, the glass transition temperature 9.9° C. and the melting point 164.5° C.

Example 7
In Situ Polymerization of a Triblock Terpolymer of Composition G/TMC/CL=73/13.5/13.5 with 45 wt. % of a Soft Segment of Composition G/TMC/CL=40/30/30.

In the first stage, 360 g of glycolide, 270 g of 1,3-dioxan-2-one and 270 g of caprolactone, together with 0.9 g of diethylene glycol and 0.2 g of tin octoate (solution in diethyl ether) are placed in the reactor. After drying for 16 h at 50° C. in high vacuum, an overpressure of 1.5 bar argon is applied and the reaction mixture is heated, accompanied by stirring, for 30 min to 205° C. This temperature is maintained for 5 h. In stage 2 there is an addition of 1100 g of melted glycolide for forming hard segments, under an argon counterflow and with vigorous stirring. Simultaneously the temperature is raised for 10 min to 230° C., then lowered to 220° C. and kept there for 90 min.

The polymer has an inherent viscosity of 1.02 dl/g, the glass transition point is 2.1° C. and the melting point 191.2° C. A sample of the soft segment taken prior to glycolide addition has an inherent viscosity of 1.081 dl/g and the glass transition point is −20.1° C.

Example 8
In Situ Polymerization of a Triblock Terpolymer of Composition G/TMC/CL=73/13.5/13.5 with 54 wt. % of a Soft Segment of Composition G/TMC/CL=50/25/25.

In the first stage, 540 g of glycolide, 270 g of 1,3-dioxan-2-one and 270 g of caprolactone, together with 1.08 g diethylene glycol and 0.216 g of tin octoate (solution in diethyl ether) are placed in the reactor. After drying for 16 h at 50° C. in high vacuum, an overpressure of 1.5 bar argon is applied and the reaction mixture is heated to 205° C. for 30 min, accompanied by stirring. This temperature is maintained for 5 h. In stage 2 1100 g of melted glycolide are added for forming the hard segments, under an argon counterflow and accompanied by vigorous stirring. Simultaneously the temperature is raised for 10 min to 230° C., then lowered to 220° C. and kept there for a further 80 min.

The polymer has an inherent viscosity of 0.99 dl/g, a glass transition point of 10.4° C. and a melting point of 183.6° C.

Example 9
Extrusion of the ABA Triblock Terpolymer to the Monofilament.

The triblock terpolymer of example 7 is melted with a twin-screw extruder at a screw speed of 21 r.p.m. and spun to monofilaments. The L/D ratio of the nozzle capillaries is 24:1. The nozzle temperature is 205° C., i.e. above the melting point of the polymer (191° C.). For strengthening purposes, the extruded polymer strand is drawn through a cooling bath with water at 20° C. The distance between the nozzle and the bath is 6 cm. The solid, monofilament thread is wound up. For stretching or drawing purposes the monofilament is subsequently passed over heated drawing rails. The first rail is heated to 30° C. and the second to 60° C. The draw ratio for the first path is 6.8:1 and for the second 1.32:1, which gives a total draw ratio of 9.0:1. In order to obtain an adequate dimensional stability, the drawn threads are then annealed in a further process stage for 5 hours at 80° C. The heat set thread is then provided, for use as a surgical suture thread, with a needle, followed by packing and sterilization. The mechanical characteristics of the thread are given in table 1.

Example 10
Extrusion of the ABA Triblock Terpolymer to the Monofilament.

The triblock terpolymer of example 8 is spun to the monofilament in accordance with example 9.

The process conditions for extrusion, drawing and annealing, together with the mechanical characteristics of the monofilaments of examples 9 and 10, are given in the following table 1.

TABLE 1

| Extrusion | Example 9 | Example 10 |
|---|---|---|
| Polymer | From Ex. 7 | From Ex. 8 |
| Screw speed (r.p.m.) | 21 | 22 |
| Nozzle temperature (° C.) | 205 | 185 |
| Nozzle pressure (bar) | 45 | 72 |
| Capillary diameter (mtn) | 1.8 | 1.8 |
| Nozzle-bath spacing (cm) | 6 | 4 |
| Bath medium | water | water |
| Bath temperature (° C.) | 20 | 20 |
| Draw-off speed (m/min) | 10.0 | 8.0 |
| Drawing | | |
| Draw ratio 1 | 6.8:1 | 6:1 |
| Temperature rail 1 (° C.) | 30 | 40 |
| Draw ratio 2 | 1.32:1 | 1.1:1 |
| Temperature oven 2 (° C.) | 60 | 80 |
| Total draw | 9.0:1 | 6.6:1 |
| Filament diameter (mm) | 0.352 | 0.472 |
| Linear tensile strength (N) | 49.5 | 73.5 |
| Knot tensile strength (N) | 34.6 | 49.3 |
| Modulus of elasticity (N/mm$^2$) | 848 | 645 |
| Elongation (%) | 29.2 | 30.3 |
| Annealing (no shrinkage) | | |
| Annealing time (h) | 5 | 10 |
| Annealing temperature (° C.) | 80 | 100 |
| Filament diameter (mm) | 0.349 | 0.472 |
| Linear tensile strength (N) | 54.4 | 75.9 |
| Knot tensile strength (N) | 35.9 | 53.4 |
| Modulus of elasticity (N/mm$^2$) | 1317.8 | 798.5 |
| Elongation (%) | 24.9 | 32.7 |

Example 11

In Situ Polymerization of a Triblock Terpolymer of Composition G/TMC/CL=72/14/14 with 38 wt. % of a Soft Segment of Composition G/TMC/CL=26/37/37.

In the first stage, 197.6 g glycolide, 281.2 g 1,3-dioxan-2-one and 281.2 g caprolactone, together with 760 mg diethylene glycol and 150 mg tin octoate (solution in diethyl ether) are placed in the reactor and polymerized in accordance with example 7, with the difference that in the second stage 1240 g of glycolide are added and the reaction temperature is subsequently raised from 205° C. to 225° C. and maintained for a further 90 min.

The inherent viscosity of the soft segment prior to glycolide addition is 0.994 dl/g and its glass transition point is −26.9° C.

The triblock terpolymer has an inherent viscosity of 0.883 dl/g and a melting point of 215.3° C. The occurrence of two separate glass transition temperatures of −16.8° C. and +28.3° C. is an indication of an at least partial incompatibility between the hard and soft segments.

Example 12

In Situ Polymerization of a Triblock Terpolymer of Composition G/TMC/CL=72/14/14 with 40 wt. % of a Soft Segment of Composition G/TMC/CL=30/35/35.

In the first stage, 240.0 g glycolide, 280.0 g 1,3-dioxan-2-one and 280.0 g caprolactone, together with 800 mg of diethylene glycol and 160 mg tin octoate (solution in diethyl ether) are polymerized with the same reaction performance as in example 10 and in the second stage reacted with 1200 g glycolide to the triblock terpolymer.

The inherent viscosity of the soft segment prior to glycolide addition is 1.112 dl/g and its glass transition point is −21.8° C.

The triblock terpolymer has an inherent viscosity of 0.91 dl/g and a melting point of 209.4° C. It is possible to detect in the DSC a single, but wide glass transition of 11.3° C.

Example 13

In Situ Polymerization of a Triblock Terpolymer of Composition G/TMC/CL=72/14/14 with 43 wt. % of a Soft Segment of Composition G/TMC/CL=35/32.5/32.5.

In the first stage, 301.0 g glycolide, 279.5 g 1,3-dioxan-2-one and 279.5 g caprolactone, together with 900 mg diethylene glycol and 180 mg tin octoate (solution in diethyl ether) in the same reaction performance as in example 10 under polymerization and are reacted in the second stage with 1140.0 g glycolide to the triblock terpolymer.

The inherent viscosity of the soft segment prior to glycolide addition is 1.144 dl/g and the glass transition point is at −19.1° C. The triblock terpolymer has an inherent viscosity of 1.036 dl/g and a melting point of 206.5° C. A single glass transition of 11.2° C. is detectable in DSC.

Example 14

In Situ Polymerization of a Triblock Terpolymer of Composition G/TMC/CL=70/15/15 with 50 wt. % of a Soft Segment of Composition G/TMC/CL=40/30/30.

In the first stage, 400 g glycolide, 300 g 1,3-dioxan-2-one and 300 g caprolactone, together with 1000 mg diethylene glycol and 200 mg tin octoate (solution in diethyl ether), are polymerized in an identical reaction performance to example 10 and reacted in the second stage with 1000 g glycolide to the triblock terpolymer.

The inherent viscosity of the soft segment prior to glycolide addition is 1.083 dl/g and the glass transition point −15.6° C. The triblock terpolymer has an inherent viscosity of 1.060 dl/g and a melting point of 186.3° C. A single glass transition of 5.1° C. is detectable in DSC.

Processing of the polymers of examples 11 to 14 to monofilaments and their characteristics.

The polymers of examples 11 to 14 were extruded in a similar manner to examples 9 and 10 to monofilaments, followed by drawing and post-treatment. Table 2 shows the mechanical characteristics of these fibres, as a function of the composition of the soft segment and its proportion in the triblock terpolymer.

TABLE 2

Influence of the compatibility between the hard and soft segments and influence of the soft segment percentage on the mechanical fibre characteristics - comparison with commercial products and patents.

| Ex. | Polym. Ex. | SS % wt. % | Glycolide in SS (wt. %) | d (mm) | LTS (N/mm$^2$) | Elong. (%) | Modulus (N/mm$^2$) | KTS (N/mm$^2$) |
|---|---|---|---|---|---|---|---|---|
| 11a | 11 | 38 | 26 | 0.500 | 476 | 38.7 | 2293 | 311 |
| 12a | 12 | 40 | 30 | 0.441 | 461 | 46.2 | 2012 | 348 |
| 13a | 13 | 43 | 35 | 0.475 | 595 | 37 | 1284 | 421 |
| 13b | 13 | 43 | 35 | 0.211 | 660 | 36.4 | 1335 | 592 |
| 13c | 13 | 43 | 35 | 0.360 | 642 | 41.7 | 1329 | 504 |
| 13d | 13 | 43 | 35 | 0.262 | 542 | 36.9 | 902 | 433 |
| 14a | 14 | 50 | 40 | 0.359 | 410 | 28.3 | 775 | 328 |
| USSG US-Pat. | | 35 | 0 | 0.301 | 383 | 21 | — | 317 |

TABLE 2-continued

Influence of the compatibility between the hard and soft segments and influence of the soft segment percentage on the mechanical fibre characteristics - comparison with commercial products and patents.

| Ex. | Polym. Ex. | SS % wt. % | Glycolide in SS (wt. %) | d (mm) | LTS (N/mm$^2$) | Elong. (%) | Modulus (N/mm$^2$) | KTS (N/mm$^2$) |
|---|---|---|---|---|---|---|---|---|
| Monocryl USP | | 0 | | 0.433 | 666 | 48.1 | 893 | 360 |
| Biosyn USP | | 0 | | 0.449 | 791 | 37.0 | 1530 | 405 |

SS = soft segment
d = thread diameter
LTS = linear tensile strength
KTS = knot tensile strength
— = no information
USSC = U.S. Pat. No. 5,431,679

TABLE 3

Influence of the soft segment percentage and total glycolide content on the in vitro degradation in the Sorensen buffer (pH 7.4 at 37° C.).

| Ex. | SS % (wt. %) | Total glycolide (wt. %) | KTS retention after 7 days (%) | KTS retention after 14 days (%) |
|---|---|---|---|---|
| 12a | 40 | 72 | 68.8 | 32.1 |
| 13a | 43 | 72 | 66.6 | 31.3 |
| 14a | 50 | 70 | 44.2 | 7.4 |
| 10 | 54 | 73 | 41.5 | 5.6 |
| Monocryl USP 0 | | | 40.0 | 15.0 |
| Biosyn USP 0 | | | 64.8 | 44.1 |

Surprisingly thread lha only has only moderate strength characteristics, although the hard segment percentage and therefore crystallinity is highest.

Consequently the incompatibility between the hard and soft segments has a negative effect on the mechanical characteristics. In addition, the comparison with the thread of U.S. Pat. No. 5,431,679, whose hard segments are also of glycolide, but whose soft segment is only of trimethylene carbonate and caprolactone, shows that in the present invention by polymerizing glycolide into the soft segment, the compatibility with the hard segment is improved and the mechanical characteristics are much better. It is also clear that an adequately low modulus, which is an indication of the flexural slackness and therefore flexibility of the thread, is obtained with a soft segment percentage of 43 wt. % or higher. However, the tensile strengths decrease on further increasing the soft segment percentage, so that the polymer composition of threads 13a to 13d represents the optimum.

On comparison of threads 12a and 13a with respect to the in vitro degradation behaviour, it is clear that there are no differences between a soft segment percentage of 40 and 43 wt. %, for the same total glycolide percentage.

As among the monomers used, glycolide gives the fastest degradable polymer, the degradation kinetics of thread 14a with a total glycolide content of only 70 wt. % are surprising. Here the reduced crystallinity due to the increase in the soft segment percentage appears to speed up degradation, which also applies for example 10.

Thus, by means of the claimed polymer compositions, the degradation kinetics can be varied within certain limits by varying a) the total glycolide content and/or b) the soft segment percentage.

On comparing the degradation kinetics of the present invention with the values of the commercial products Monocryl (Eticon) and Biosyn (USSC), it can be seen that the range between them can be covered. The longer degradation time compared with Monocryl in the preferred embodiment of the invention is particularly advantageous if a delayed wound healing process occurs.

What is claimed is:

1. A surgical suture material comprising a triblock terpolymer having an ABA structure formed from a biodegradable hard segment A and a biodegradable soft segment B, in which the soft segment B is dihydroxy-terminated and chemically bound to the two hard segments A, wherein the soft segment B is a random terpolymer having an amorphous structure, the hard segment blocks A contains a glycolide monomer and represents 20 to 95 weight % of the triblock terpolymer, the terpolymer of the soft segment B being formed from trimethylene carbonate, $\epsilon$-caprolactone and glycolide, with the trimethylene carbonate present in an amount of 5 to 70 weight %, the $\epsilon$-caprolactone present in an amount of 5 to 70 weight % and the glycolide present in an amount of 10 to 70 weight %, and with the trimethylene carbonate and $\epsilon$-caprolactone being present in a weight ratio of between 80:20 and 20:80, wherein the terpolymer has a glass transition temperature in the range of −10 to +25° C. and a melting point which is at least 164.5° C.

2. The surgical suture material according to claim 1, wherein the hard segment block represents 40 to 60 weight % of the triblock terpolymer.

3. A surgical suture material wholly or partly formed from a triblock terpolymer according to claim 2.

4. The surgical suture material of claim 3 in the form of a monofilament or multifilament thread.

5. The surgical suture material of claim 1 in the form of a monofilament or multifilament thread.

6. A process for the production of a surgical suture material comprising a triblock terpolymer having an ABA structure of a biodegradable hard segment A and a biodegradable soft segment B, wherein the soft segment is a dihydroxy-terminated random terpolymer with an amorphous structure and wherein the terpolymer has a glass transition temperature in the range of −10 to +25° C. and a melting point which is at least 164.5° C., comprising the steps of:

preparing the soft segment B by statistically copolymerizing 5 to 70 weight percent trimethylene carbonate, 5 to 70 weight percent $\epsilon$-caprolactone and 10 to 70 weight percent glycolide, wherein the weight ratio of trimethylene carbonate and $\epsilon$-caprolactone is between 80:20 and 20:80, optionally in the presence of a catalyst or a bifunctional initiator, at a temperature above 150° C. so that the mixture is a melt, with stirring and with an over pressure of between 1 and 2 bars for a sufficient time to produce the soft segment;

recovering the dihydroxy-terminated soft segment;

chemically reacting the dihydroxy-terminated soft segment with glycolide by repeated melting of the soft segment with glycolide at a temperature of between 200 and 250° C., optionally in the presence of a catalyst or a bifunctional initiator, with stirring and with an over pressure of between 1 and 2 bars, for a sufficient time to produce the triblock terpolymer; and recovering the triblock terpolymer as the suture material.

7. The process according to claim 6, wherein the soft segment is produced by random copolymerization of trimethylene carbonate, ε-caprolactone and glycolide, containing 10 to 40 weight % trimethylene carbonate, 10 to 40 weight % ε-caprolactone and 30 to 50 weight % glycolide.

8. The process according to claim 6, wherein the triblock terpolymer is treated with γ rays to shorten the degradation time of the polymer.

9. The process according to claim 6, wherein the soft segment is recovered by discharging the soft segment from the reactor, cooling the soft segment, comminuting the soft segment and then drying the soft segment, and the triblock terpolymer is recovered by discharging the triblock terpolymer from the reactor, cooling the triblock terpolymer, comminuting the triblock terpolymer, and then drying triblock terpolymer.

10. A process for the production of a surgical suture material comprising a triblock terpolymer having a structure ABA having a biodegradable hard segment A and a biodegradable soft segment B, wherein the soft segment is a dihydroxy-terminated random terpolymer with a completely amorphous structure and wherein the terpolymer has a glass transition temperature of −10 to +25° C. and a melting point of at least 164.5° C., comprising the steps of:

preparing the soft segment B in a polymerization reactor by statistically copolymerizing 5 to 70 weight percent trimethylene carbonate, 5 to 70 weight percent ε-caprolactone, and 10 to 70 weight percent glycolide, wherein the weight ratio of trimethylene carbonate and ε-caprolactone is between 80:20 and 20:80, optionally in the presence of a catalyst or a bifunctional initiator, at a temperature between 200 and 210° C. so that the mixture is a melt with stirring and with an over pressure of between 1 and 2 bars for a sufficient time to produce the soft segment;

chemically reacting the dihydroxy-terminated soft segment with glycolide by adding to the melted soft segment in the polymerization reactor glycolide monomer as a melt under an argon counterflow, with vigorous stirring, raising the temperature to about 230° C. in less than 15 minutes, reducing the temperature to 220° C. and allowing the reaction to proceed for sufficient time to form the triblock terpolymer; and recovering the triblock terpolymer as the suture material.

11. The process according to claim 10, wherein the soft segment is produced by random copolymerization of trimethylene carbonate, ε-caprolactone and-glycolide, containing 10 to 40 weight % trimethylene carbonate, 10 to 40 weight ε-caprolactone and 30 to 50 weight % glycolide.

12. The process according to claim 10, wherein the triblock terpolymer is treated with γ rays to shorten the degradation time of the polymer.

13. The process according to claim 10, wherein the triblock terpolymer is recovered by discharging the triblock terpolymer from the reactor, cooling the triblock terpolymer, comminuting the triblock terpolymer, and the drying triblock terpolymer.

* * * * *

UNITED STATES PATENT AND TRADEMARK OFFICE
CERTIFICATE OF CORRECTION

PATENT NO. : 6,048,947
DATED : April 11, 2000
INVENTOR(S) : Sven Oberhoffner et al.

It is certified that error appears in the above-identified patent and that said Letters Patent is hereby corrected as shown below:

Title page:
"[30] Foreign Application Priority Data": change foreign application priority date from "August 10, 1996" to --October 8, 1996--.

Column 16:
Line 25, (claim 11, line 5): change "weight ε-caprolactone" to --weight % ε-caprolactone--.

Signed and Sealed this

Nineteenth Day of June, 2001

Attest:

NICHOLAS P. GODICI
Attesting Officer    Acting Director of the United States Patent and Trademark Office